United States Patent [19]

Filip et al.

[11] Patent Number: 5,103,556
[45] Date of Patent: Apr. 14, 1992

[54] METHOD OF MANUFACTURING AN ELECTROHYDRAULIC PROBE

[75] Inventors: Mihail Filip, Shelton; Frank D. D'Amelio, Oxford, both of Conn.

[73] Assignee: Circon Corporation, Santa Barbara, Calif.

[21] Appl. No.: 583,583

[22] Filed: Sep. 14, 1990

Related U.S. Application Data

[62] Division of Ser. No. 198,846, May 5, 1988, abandoned.

[51] Int. Cl.⁵ .......................................... H01R 43/00
[52] U.S. Cl. ....................................... 29/825; 29/828; 606/128
[58] Field of Search ................... 29/828, 825; 128/328; 606/128

[56] References Cited

U.S. PATENT DOCUMENTS

| | | | |
|---|---|---|---|
| 3,313,293 | 4/1967 | Chesebrough et al. | 128/303.18 |
| 3,413,976 | 12/1968 | Roze | 128/328 |
| 3,543,757 | 1/1970 | Balaey et al. | 128/328 |
| 3,735,764 | 5/1973 | Balev et al. | 128/328 |
| 3,785,382 | 1/1974 | Schmidt-Kloiber | 128/328 |
| 3,792,701 | 2/1974 | Kloz et al. | 128/7 |
| 3,823,717 | 7/1974 | Pohlman et al. | 128/305 |
| 3,830,240 | 8/1974 | Antonevich et al. | 128/328 |
| 3,861,391 | 1/1975 | Antonevich et al. | 128/328 |
| 4,026,726 | 5/1977 | Carney | 128/419 P |
| 4,027,674 | 6/1977 | Tessler et al. | 128/328 |
| 4,030,505 | 6/1977 | Tessler | 128/328 |
| 4,034,762 | 7/1977 | Cosens et al. | |
| 4,059,330 | 11/1977 | Shirey | 29/828 X |
| 4,548,207 | 10/1985 | Riemels | 128/303.18 |
| 4,582,057 | 4/1986 | Auth et al. | 128/303.1 |
| 4,643,186 | 2/1987 | Rosen et al. | 128/303.13 |
| 4,658,836 | 4/1987 | Turner | 128/642 |
| 4,663,234 | 5/1987 | Bouton | 428/422 |
| 4,674,499 | 6/1987 | Pao | 128/303.17 |
| 4,712,296 | 12/1987 | Forner, Jr. et al. | 29/828 |

FOREIGN PATENT DOCUMENTS 2829159  1/1980  Fed. Rep. of Germany ... 128/328 S

OTHER PUBLICATIONS

"Elektrische Lithotripsie Mit Urat-1", by Dr. H. J. Reuter, Medizinal-Markt/ACTA Medicotechnica, 1986, pp. 414-415.
Electronics Engineer's Handbook, 2nd Edition, Tink and Christianson, Table 9-5, "Dielectric Materials", pp. 9-12, 1982.

*Primary Examiner*—Carl J. Arbes
*Attorney, Agent, or Firm*—Daniel J. Meaney, Jr.

[57] ABSTRACT

A method of manufacturing an electrohydraulic probe for use with a lithotriptic instrument is shown. The probe comprises a first electrode, a second electrode and a relatively rigid spacer means therebetween to maintain a relatively constant equidistant space between the first and second electrodes during the entire work life of the probe. The method comprises the steps of connecting a distal end spacer member with a first electrode wherein the spacer member has a central aperture therein with a relatively constant thickness between its central aperture and an outer perimeter of the space member at the distal tip of the probe and wherein the spacer member comprises a relatively mechanically rigid dielectric material; and connecting a second electrode with the spacer member wherein the central aperture such that said second electrode is spaced equidistantly from the first electrode at the distal tip of the probe.

12 Claims, 2 Drawing Sheets

METHOD OF MANUFACTURING AN ELECTROHYDRAULIC PROBE

This is a division of application Ser. No. 07/198,846 filed May 5, 1988, now abandoned.

1. Field of the Invention

The present invention relates to electrohydraulic instruments and, more particularly, to a probe for use with a lithotriptoscope and a method of making the same.

2. Prior Art

Electrohydraulic instruments can generally be described as instruments that produce hydraulic shock waves through electrical discharges in a liquid dielectric medium. The production of shock waves by means of electrohydraulics has been put to use in lithotriptic probes for the destruction of vesical calculi or stones in the bladder, ureter and kidneys. Various different means for the treatment of stones can be found in the following U.S. Pat. Nos.; U.S. Pat. No. 3,785,382 by Schmidt-Kloiber et.al;. U.S. Pat. No. 3,543,757 by Balev et al; U.S. Pat. No. 4,027,674 by Tessler et al; U.S. Pat. No. 3,792,701 by Kloz et al; U.S. Pat. No. 3,823,717 by Pohlman et al; U.S. Pat. No. 3,830,240 by Antonevich et al. and U.S. Pat. No. 3,413,976 by Roze.

The distal tips of electrohydraulic lithotripsy probes have generally taken two types of configurations; two electrodes arranged side-by-side or an inner electrode surrounded by an outer coaxial electrode. In both configurations, one electrode would discharge an electric current to the other electrode in the form of a flashover or dielectric breakdown through the dielectric liquid. The strength of the shockwave is generally directly proportional to the distance between the two electrodes. The greater the distance between electrodes, the greater the voltage needed to cause the breakdown of the dielectric liquid and thus, the stronger the resulting shockwave at breakdown.

However, problems exist with the probes used in the prior art. In particular, in the manufacture of probes having the inner and outer electrode configuration, it has not been possible to manufacture the two electrodes with an equispaced distance therebetween that is maintained throughout the entire work life of the probe. In the probes of the prior art, the dielectric material between the inner and outer electrodes is merely the outer covering of the inner electrode. Ordinarily, the inner electrode is a conductive wire with a soft and flexible insulation cover typical of an electrical wire. Because of the high temperatures and pressures generated at the probe distal tip, during operation of the probe, the dielectric material separating the two electrodes softens resulting in movement between the two electrodes. Failure to provide and maintain an equal distance between the inner electrode and outer electrode results in the flashover occurring along a predominate path, the shortest distance between the electrodes, rather than the desired multiple various flashover paths. The resulting predominate flashover path causes premature inner dielectric breakdown and eventual failure along the flashover line, thus causing pitting and burning at a single area on the outer electrode reducing the working life of the probe. This reduction in the working life of the probe is typically due to two types of failures. First, the inner dielectric can experience breakdown due to more frequent flashovers about a specific point or area. These frequent concentrated flashovers form a more conductive line that allow flashovers to occur at increasingly low voltages. This results in greatly reducing the effectiveness of the shock-wave. Second, the concentrated flashovers caused by the non-centered electrodes can result in the inner dielectric experiencing actual mechanical failure such as a fracture or split of the inner dielectric material proximate the flashover line. This generally allows the inner electrode to move relative to the outer electrode decreasing the spacing between the electrodes. This decrease in spacing reduces the strength of resulting shockwaves and can eventually result in the two electrodes coming into contact and causing an electrical short with a resulting total failure of the probe.

It is an objective of the present invention to provide a probe for use with an electrohydraulic device that will have a substantially longer worklife than prior art probes.

It is a further objective of the present invention to provide a probe with an inner electrode and an outer electrode that can maintain an equispaced distance therebetween for the entire work life of the probe.

It is a further objective of the present invention to provide a quick and accurate method for producing probes with an inner electrode and outer equispaced electrode.

SUMMARY OF THE INVENTION

The foregoing problems are overcome and other advantages are provided by a probe for electrohydraulically impacting objects having at least two electrodes and a relatively rigid dielectric spacer therebetween.

In accordance with one embodiment of the invention a probe is provided comprising a first electrode means; a second electrode means spatially disposed relative to the first electrode means at a distal tip of the probe with a relatively constant distance therebetween and forming multiple electrical jumpways therebetween; and a spacer means disposed between the first and second electrode means. The spacer means comprises a relatively rigid dielectric material such that the first and second electrode means are positioned and maintained at a relatively precise and constant distance therebetween whereby the jumpways are substantially similar to prevent a jumpway from being predominantly used over other jumpways.

In accordance with another embodiment of the invention an electrohydraulic lithotriptoscope is provided with a probe having a distal working end. The distal working end comprises an inner electrode, a spacer means fixedly connected to the inner electrode and an outer electrode. The spacer means comprises a first tube member comprised of a rigid dielectric material having at least a portion of the inner electrode disposed therein and forming an outer perimeter equispaced from the inner electrode. The outer electrode comprises a second tube member having at least a portion of its inner diameter proximate the spacer means outer perimeter whereby the spacer means provides a rigid insulative barrier between the inner and outer electrodes while maintaining a constant separative distance therebetween proximate the distal end.

In accordance with one method of the invention a method is provided for manufacturing a electrohydraulic probe for use with a lithotriptic instrument comprising the steps of connecting a distal end spacer means with a first electrode and connecting a second electrode with the spacer means. The spacer means has a central aperture therein with a relatively constant thickness between the central aperture and an outer perimeter of the spacer means at the distal end of the probe. The spacer means is comprised of a rigid dielectric material and is in contact with the first electrode about its outer perimeter. The second electrode is disposed in the central aperture of the spacer means such that the second electrode is rigidly equispaced from the first electrode at the distal end of the probe.

BRIEF DESCRIPTION OF THE DRAWINGS

The foregoing aspects and other features of the invention are explained in the following description, taken in connection with the accompanying drawings wherein.

DETAILED DESCRIPTION OF THE INVENTION

Figure 1:
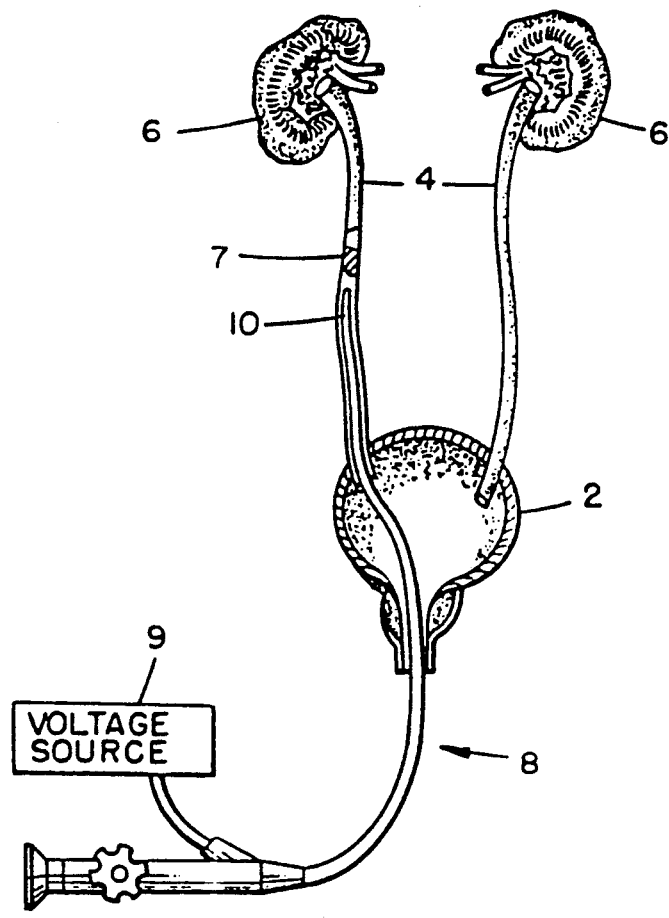
FIG. 1 is a diagrammatical view of an inspection instrument for electrohydraulically impacting objects in use in the ureter of a patient.

Referring to FIG. 1 there is shown a diagrammatical view of the bladder 2, ureter 4 and kidney 6 areas of a patient having a lithotriptoscope 8 moving therein. Although the following description is being given with reference to a lithotriptoscope, it is to be understood that the present invention can be used with any suitable type of instrument. The lithotriptoscope 8 is generally provided for accessing the ureter area of a patient for the destruction of vesical calculus 7. The lithotriptoscope, in this embodiment, has a probe 10 which uses electrohydraulics to impact the calculus 7 and for this purpose has a voltage source or generator 9 connected thereto. The probe 10, in this embodiment, passes through a working channel (not shown) of the lithotriptoscope 8 and has a distal working end 14 (See FIG. 2) that is extendable from an aperture (not shown) at the distal end of the lithotriptoscope 8.

Figure 2:
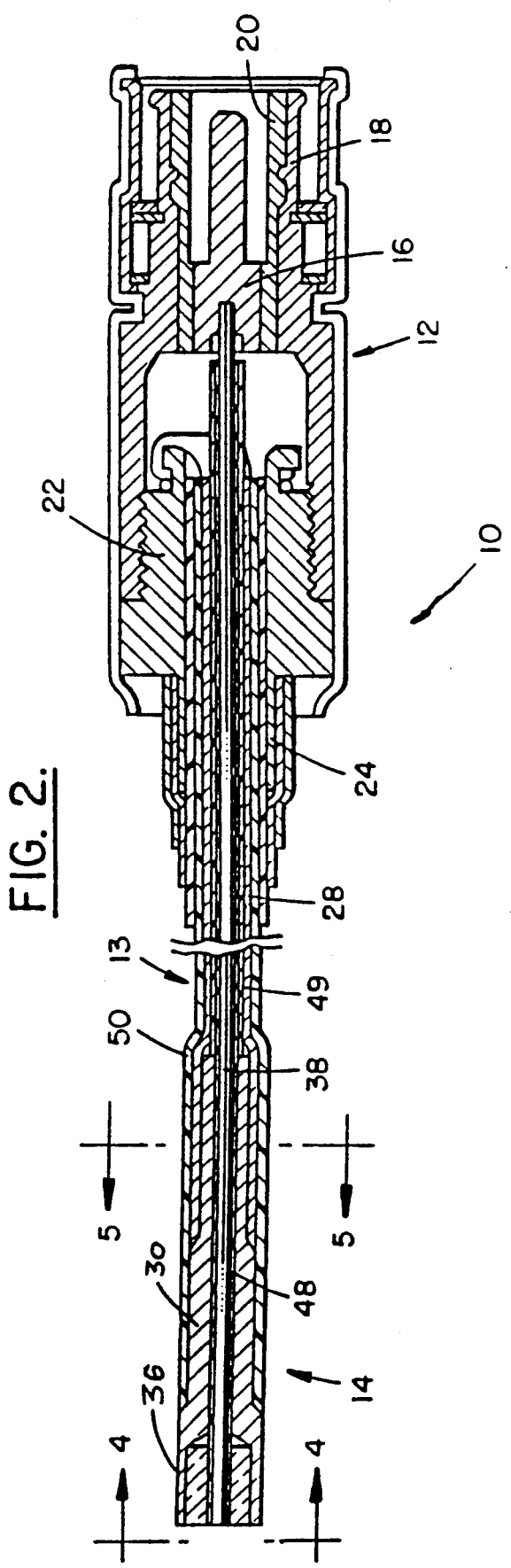
FIG. 2 is a cross-sectional view of a probe incorporating features of the invention.
Figure 5:
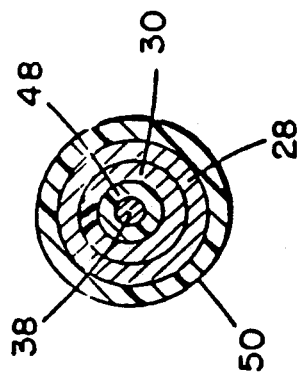
FIG. 5 is a cross-sectional view of the shaft section of the probe taken along lines 5—5 of FIG. 2.

Referring now also to FIG. 2, a cross-sectional view of the probe 10 incorporating features of the invention is shown. The probe 10, in this embodiment, is connectable to the voltage source 9 via a coaxially connector in a body section 12 of the probe 10. In an alternative embodiment, the probe 10 may be integrally formed with the lithotriptoscope. The probe 10, in this embodiment, generally comprises a body section 12, a shaft section 13 and a distal end 14. The shaft section 13, in this embodiment, generally comprises two conductors comprised of an outer sheath 28 and an inner wire 38. The outer sheath 28 is generally concentrically disposed relative to the inner wire 38. Located between the two conductors 28 and 38 are a cover 48 of dielectric material and a stiffener 49 made of any suitable material. The stiffener 49 provides a stiffness to the shaft section 13. An exterior coating 50 is provided around the sheath 28 to protectively insulate the sheath 28 as well as the patient. The inner conductor 38 may be made of any suitable material such as copper and is preferably provided as a solid wire. The dielectric material 48 between the inner conductor 38 and the outer conductor 28 may also be made of any suitable material. Preferably, the dielectric material 48 is resistant to chemical solvents and has a high dielectric strength, such as a polyimide resin.

Preferably, the inner conductor 38 and the dielectric material 48 are provided as a unitary member with the dielectric material 48 acting as a protective insulative cover for the inner conductor 38. The outer conductor 28 can generally be described as a tube shaped member. Preferably, the outer conductor 28 is comprised of a wire braid sheath.

The body section 12 is generally comprised of an inner connector 16, an outer connector 18, an insulation barrier 20 therebetween and a second outer connector 22. A portion of the shaft section 13 passes through a central aperture 24 in the second outer connector 22. Inside the body section 12, the inner conductor 38 and the outer sheath 28 are separated. A portion of the insulation 48 covering inner conductor 38 is stripped therefrom and the inner conductor is fixedly and electrically connected to the inner connector 16. The wire braid sheath 28 passes into a chamber formed between the first outer connector 18 and the second outer connector 22 and makes an electrical contact therewith as well as being relatively fixedly held therein.

Figure 3:
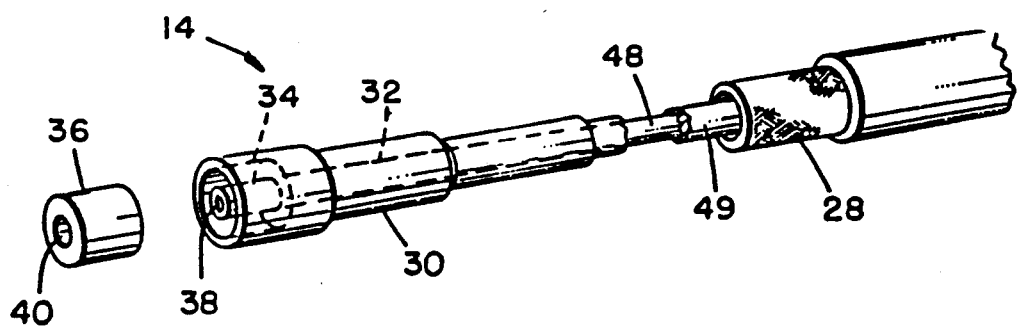
FIG. 3 is an exploded view of the distal end of the probe shown in FIG. 2.

Referring now also to FIG. 3, an exploded view of the distal end 14 of the probe 10 is shown. The distal end of the probe 10 generally comprises the first electrode 30 which is electrically connected to the outer sheath 28, a spacer 36 and the inner conductor 38 which forms a second electrode. The first electrode or outer electrode 30 is generally comprised of a metallic material and has an internal passage 32 therethrough. Located at the tip of the first electrode 30 is an enlarged area of the passage 32 forming an internal seat 34. The exterior of the electrode 30, in this embodiment, is generally circular in cross section having three different outer diameters which narrow in size from the tip. The seat 34 is also generally circular in cross section such that the second electrode 38 forms a ring shape at the distal tip as shown in FIG. 4.

The spacer 36 is generally comprised of a dielectric material capable of preventing electrical current flow through the spacer between the first electrode 30 and the inner conductor or second electrode 38. The spacer 36, in this embodiment, is generally a tube shaped member having an outer diameter slightly larger than the diameter of the seat 34. The spacer 36 also has a central aperture 40 to allow for passage of the inner conductor 38 therethrough. The size of the central aperture 40 is slightly larger than the size of the inner conductor 38, but slightly smaller than the size of the inner conductor 38 with the dielectric material or cover 48 therearound. In this embodiment, the spacer is comprised of a rigid or semi-rigid material such as VESPEL, a trademark of E.I. Dupont Corporation, a polyimide resin. However, any suitable relatively rigid dielectric material that can withstand high temperatures and pressures can be used. The thickness of the spacer 36 between the central aperture 40 and its outer diameter is relatively constant such that the spacing between the inner conductor 38 and the outer electrode 30 is substantially identical and uniform around the entire tip. Because the spacer 36 is made of a relatively rigid material, the probe 10 can be manufactured such that the distance between the inner conductor 38 and the outer electrode 30 is relatively precise and accurate to allow for a uniform equispaced distance between the two electrodes such as by machining the central aperture 40 concentric relative to the outer diameter.

The assembly of the distal end 14 of the probe 10 generally comprises the following steps. The spacer 36 is placed adjacent the distal tip of the first electrode 30 and aligned therewith. Because the spacer 36 has an outer diameter slightly larger than the inner diameter of the seat 34 of the first electrode 30, a predetermined force is applied to the spacer 36 and first electrode 30 to press fit the spacer 36 into the seat 34 slightly compacting or compressing the spacer therein. The spacer 36, due to its compression, is relatively fixedly held in the seat 34. In an alternative embodiment, the spacer 36 and seat 34 may be provided with cooperating threads such that the spacer 36 can be screwed into the seat 34. However, any suitable fixation means can be used. A portion of the stiffener 49 is removed from the distal end of the stiffener 49 such that when finally assembly, the stiffener 49 will not be located in the central aperture 40 of the spacer 36 or interfere with the passage of the inner conductor 38 or cover 48 through the central aperture 40 as will be evident from the description below. A portion of the dielectric cover 48 surrounding the first conductor 38 is stripped from the distal end of the conductor. The distal end of the conductor 38 having its insulation removed can now be passed through the inner passage 32 of the outer elements 30 and through the central aperture 40 in the spacer 36. As the inner conductor 38 passes through the central aperture 40 the dielectric cover 48 surrounding the inner conductor 38 eventually comes into contact with the spacer 36 and because of the larger diameter of the cover 48 surrounding the inner conductor relative to the central aperture 40. the dielectric material of the cover 48 prevents the inner conductor 38 from being further advanced without additional force. At this point, additional force is provided to advance the spacer along the inner conductor 38 with the insulation material of the cover 48 being compressed or wedged within the central aperture 40 of the spacer 36. The inner conductor 38 and cover 48 are advanced a predetermined distance until at least a portion of the cover 48 of the inner conductor 38 passes completely through the central aperture 40. The stiffener 49, having its distal end previously trimmed a predetermined distance, does not interfere with the passage of the inner conductor 38 and cover 48 through the spacer 36. The inner conductor 38 and its insulation cover 48 are trimmed from a first end of the spacer 36 which will form the distal tip of the probe 10. The inner conductor 38 is fixedly held inside the central aperture 40 of the spacer due to the compacted nature of its cover 48 therein. Thus, the distal end of the probe 10 can be assembled without the use of additional fixation means. The wire braid or sheath 28 is electrically connected to the outer electrode 30. Thus manufactured, the inner connector 16 in the body section 12 is electrically connected to the inner conductor 38 which forms the second electrode at the distal tip and the outer connector 18 in the body section 12 is also electrically connected to the first electrode 30 at the distal tip whereby a voltage applied to the inner connector 16 can travel tot he distal tip of the inner conductor 38 and jump across the spacer 36 at the distal tip to the outer electrode 30 which allows the voltage to travel back to the outer connector 18 and back into the voltage source 9.

Figure 4:
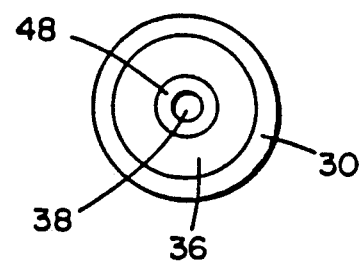
FIG. 4 is a plane end view of the probe tip taken along lines 4—4 of FIG. 2.

Referring now also to FIG. 4, a plane view of the distal tip of the probe 10 is shown. As shown, the distal tip of the probe 10 generally appears to have a bulls-eye type shape. The inner conductor 38 formed the center of the bulls-eye surrounded by its protected insulation cover 48. Coaxially mounted with the inner conductor 38 is the spacer 36. Coaxially surrounding the spacer 36 is the first electrode 30. By the use of a rigid or semi-rigid material in manufacturing of the spacer 36 the inner conductor 38 which forms the second electrode is equispaced from the first electrode 30. When an electrical charge is sent through the second conductor 38 it will seek the path of least resistance. The probe 10 provides the path of least resistance via the second electrode 30. However, due to the fact that the second conductor 38 is relatively equally spaced from the first electrode 30 the exact path or jumpway which the current or flashover must take at the distal tip between the inner conductor 38 and the first electrode 30 is unpredictable. Because these pathways or jumpways are unpredictable, no single pathway or jumpway is predominant. Therefore, the normal pitting or scoring of the first electrode 30 due to the jumps or flashovers of electricity from the inner electrode 38 to the outer electrode 30 is evenly distributed along the entire tip of the outer electrode 30. The relatively rigid nature of the spacer substantially prevents or reduces the rate of breakdown of the spacer dielectric material and mechanical failure as described above and allows for a longer useful work life of the probe 10.

It should be understood that the foregoing description is only illustrative of the invention. Various alternative and modifications can be devised by those skilled in the art without departing from the spirit of the invention. Accordingly, the present invention is intended to embrace all such alternatives, modifications and variances which fall within the scope of the appended claims.

What is claimed is:

1. A method of manufacturing an electrohydraulic probe for use with a lithotriptic instrument comprising the steps of:
   connecting a distal end spacer means with an outer electrode, said spacer means having a central aperture therein with a relatively constant thickness between said central aperture and an outer perimeter of said spacer means at the distal tip of the probe, said spacer means comprising a relatively rigid dielectric material; and
   connecting an inner electrode with said spacer means, said inner electrode being disposed in said central aperture such that sad inner electrode is rigidly equispaced from the outer electrode at the distal tip of the probe.

2. A method as in claim 1 further comprising the step of press fitting the inner electrode into the spacer means.

3. A method as in claim 1 wherein the step of connecting said spacer means with said outer electrode comprises press fitting the spacer means onto the distal end of said outer electrode.

4. The method of claim 1 further comprising the step of:
   aligning a distal end spacer means with the outer electrode.

5. The method of claim 1 wherein the step of connecting a distal end spacer means with the inner electrode includes the step of:

applying a predetermined force to the distal end spacer means to press fit the distal end spacer means into a seat located rearward of the outer electrode and inner electrode to slightly compress the distal end spacer means between the outer electrode and the inner electrode.

6. The method of claim 1 wherein said lithotriptoscope instrument includes a distal end and stiffener which extends to the distal end, said method further comprising the step of:

removing a portion of the stiffener located at the distal end to avoid contact between the stiffener and the outer electrode and inner electrode.

7. The method of claim 1 wherein said lithotriptoscope instrument includes means defining an inner passageway which communicates with the inner electrode, said method further comprising the step of:

stripping a portion of a dielectric cover from the distal end of an electrical connector; and passing the stripped portion of the electrical conductor into the inner passageway until physical contact is made with said outer electrode to form an electrical connection therebetween.

8. The method of claim 1 wherein said lithotriptoscope instrument includes an electrically conductive sheath, said method further comprising the step of:

electrically connecting the electrically conductive sheath to the inner electrode.

9. The method of claim 1 further comprising the step of:

forming a uniform equispaced distance between the outer electrode and the inner electrode by machining the distal end spacer means to form a central aperture which is concentric relative to its outer diameter.

10. A method for destroying vesical calculi or stones in the bladder, ureter or kidney comprising the steps of:

applying a known discharge voltage to a lithotriptoscope probe which includes an inner electrode located at a distal end of the probe, an outer electrode spatially dispersed relative to and surrounding the inner electrode and positioned at a preselected space therefrom defining a controlled discharge path therebetween, and an insulating means positioned with and enclosing the space between the inner electrode and outer electrode wherein the insulating means is formed of a relatively mechanically rigid material having a dielectric constant that prevents a controlled discharge through the insulating means to cause an electrical discharge shock to occur only across said controlled discharge path which generates and applies a hydraulic shock wave to the vesical calculi or stones to disintegrate the same.

11. The method of claim 10 wherein a controlled discharge path extends between a first electrode and second electrode which is coplanar therewith and which are located at the distal end of the lithotriptoscope probe, said method further comprising the step of:

defining with the inner electrode and outer electrode a uniformly spaced controlled discharge path which extends between the inner electrode, the outer electrode and across the insulating means located at the distal end of the lithotriptoscope probe causing each generation of subsequent electrical discharges to occur only across the controlled discharge path.

12. A method of manufacturing an electrohydraulic probe for use with a lithotriptic instrument comprising the steps of:

connecting a distal end spacer means with a first electrode by threading the distal end spacer means by a co-acting threading means onto the first electrode to rotationally advance and position the distal end spacer means into a seat located rearward of the first electrode compressing the distal end spacer end means, said spacer means having a central aperture therein with a relatively constant thickness between said central aperture and an outer perimeter of said spacer means at the distal tip of the probe, said spacer means comprising a relatively rigid dielectric material; and connecting a second electrode with said spacer means, said second electrode being disposed in said central aperture such that said second electrode is rigidly equispaced from first electrode at the distal tip of the probe.

* * * * *